(12) United States Patent
Nakao et al.

(10) Patent No.: US 8,722,909 B2
(45) Date of Patent: May 13, 2014

(54) ANTIPROTOZOAL COMPOUND DERIVED FROM COELENTERATA

(75) Inventors: Yoichi Nakao, Tokyo (JP); Shintaro Ishigami, Tokyo (JP); Yasuyuki Goto, Tokyo (JP); Shin-ichiro Kawazu, Hokkaido (JP); Noboru Inoue, Hokkaido (JP)

(73) Assignee: Waseda University, Tokyo (JP)

( * ) Notice: Subject to any disclaimer, the term of this patent is extended or adjusted under 35 U.S.C. 154(b) by 0 days.

(21) Appl. No.: 13/583,789

(22) PCT Filed: Mar. 10, 2011

(86) PCT No.: PCT/JP2011/055715
§ 371 (c)(1),
(2), (4) Date: Sep. 10, 2012

(87) PCT Pub. No.: WO2011/111804
PCT Pub. Date: Sep. 15, 2011

(65) Prior Publication Data
US 2013/0005798 A1    Jan. 3, 2013

(30) Foreign Application Priority Data
Mar. 11, 2010    (JP) ................................ 2010-055150

(51) Int. Cl.
*C07D 311/00*    (2006.01)

(52) U.S. Cl.
USPC ...................................................... 549/396

(58) Field of Classification Search
USPC ...................................................... 549/396
See application file for complete search history.

(56) References Cited

FOREIGN PATENT DOCUMENTS

| JP | 2007161902 A | 6/2007 |
|----|--------------|--------|
| WO | 9632388 A1 | 10/1996 |
| WO | 2008109717 A1 | 9/2008 |

OTHER PUBLICATIONS

Iwagawa et al. Tetrahedron, 1996, 13121-13123.*
Ishigami et al. J. Org. Chem. 2012, 77, 10962-10966.*
Hooper, Gergory J., "New Metabolites from the South African Soft Coral", Tetrahedron, vol. 51, No. 36, pp. 9973-9981, 1945.
Kaminsky, R., et al., "Time-dose response of Trypanosoma congolense bloodstream forms to diminazene and isometamidium", Veternary Parsitology 52 (1994) 235-242.
Okuno, T., et al., "Applications of Recombinant Leishmania amazonensis Expressing egfp or the b-Galactosidase Gene for Drug Screening and Histopathological Analysis", Ext. Anim. 52(2), 109-118, 2003.
Konig, G., et al., "Diterpenes From the Brown Alga Dictyota Divaricata". Phytochemistry, vol. 30, No. 11, pp. 3679-3681, 1991.
Schwartz, R.E., et al., "The Coraxeniolides, Constituents of Pink Coral, Corallum SP". Tetrahedon, vol. 37, No. 16, pp. 2725-2733. 1981.
Iwagawa, T., et al., "New Xenia Diterpenoids from a Xenia Species of a Soft Coral", Tetrahedron, vol. 52, No. 41, pp. 13121-13128, 1996.
"Bruceantin, a New Potent Antileukemic Simaroubolide from Brucea antidysenterica", J. Org. Che., vol. 38, No. 1, 1973.
International Search Report mailed Apr. 5, 2011; International Application No. PCT/JP2011/055715, in the name of Waseda University and Obihiro University of Agriculture and Veterinary Medicine.
Vermeersch, M., et al., "In Vitro Susceptibilities of Leishmania donovani Promastigote and Amastigote Stages to Antileishmanial Reference Drugs: Practical Relevance of Stage Specific Differences", Antimicrobial Agents and Chemotherapy, Sep. 2009, p. 3855-3859, vol. 53, No. 9.

* cited by examiner

*Primary Examiner* — Nizal Chandrakumar
(74) *Attorney, Agent, or Firm* — Fox Rothschild, LLP; Robert J. Sacco

(57) ABSTRACT

The object is to develop an antiprotozoal remedy having a novel mechanism of action. Provided is a compound represented by a chemical formula (1), a prodrug or a pharmaceutically acceptable salt thereof, wherein within the formula (1), $R_1$ represents $R_{10}$— of formula (4) or $R_{20}$— of formula (5); $R_2$ represents CHO—, etc.; $R_3$ represents a hydrogen atom, $CH_3$—C(=O)—, etc.; $R_4$ represents a hydrogen atom, $CH_3$—C(=O)—, etc.; each of $R_{11}$ and $R_{12}$ independently represents a hydrogen atom, a methyl group, etc.; $R_{13}$ represents —$CH_2$—, —CH(—OH)— or —C(=O)—; each of $R_{21}$ and $R_{22}$ independently represents a hydrogen atom, a methyl group, etc.; $R_{23}$ represents —$CH_2$—, —CH(—OH)— or —C(=O)—; and $R_{24}$ represents a hydrogen atom, a hydroxyl group, a methyl group, etc.

5 Claims, 5 Drawing Sheets

C07110 (*A.cristata* 90 g. wet wt)
- MeOH
- H₂O / CHCl₃, n-BuOH
- 90% MeOH / n-hex
- 60% MeOH / CHCl₃

2-3 (315.9 mg)
- ODS flash column chromatog.
  - 50, 70% MeOH, 70, 85% MeCN
  - MeOH, CHCl3:MeOH:H₂O (6:4:1)

3-2 (76.8 mg)
- 71.2 mg separated
- RP-HPLC (COSMOSIL5C₁₈-AR-II φ 2×25cm, 6mL/min, 70-90% MeOH)

5-10 (cristaxenicin A 19.7 mg)

FIG.1

C07110 (*A.cristata* 90 g. wet wt)
- MeOH
- H₂O / CHCl₃, n-BuOH
- 90% MeOH / n-hex
- 60% MeOH / CHCl₃

2-3 (315.9 mg)
- ODS flash column chromatog.
  - 50, 70% MeOH, 70, 85% MeCN
  - MeOH, CHCl3:MeOH:H₂O (6:4:1)

3-3 (47.3 mg)
- RP-HPLC (COSMOSIL5C₁₈-AR-II φ 2×25cm, 8mL/min, 70-90% MeOH)

12-3 (2.5 mg)   12-7 (cristaxenicin A 3.4 mg)   12-10 (1.2 mg)

※ Approximately half separated
RP-HPLC
(COSMOSIL5C₁₈-AR-II φ 1×25cm,
2mL/min, 50-70% MeOH)

※ Approximately half separated
RP-HPLC
(COSMOSIL5C₁₈-AR-II φ 1×25cm,
2mL/min, 65-75% MeOH))

13-2 (0.2 mg)   13-4 (0.3 mg)   14-1 (0.8 mg)   14-2 (0.2 mg)
(Compound A)   (Compound B)   (cristaxenicin A)   (Compound C)

FIG.2

| atom | δ¹³C | δ¹H, m(J, Hz) | COSY | HMBC |
|---|---|---|---|---|
| 1 | 94.5 | 5.86 d (9.5) | H-11a | 1-OAc |
| 3 | 154.6 | 7.68 s | | C-1,C-4,C-4a,C-12 |
| 4 | 120.2 | | | |
| 4a | 35.9 | 3.04 m | H-5,H-5',H-11a | |
| 5 | 30.0 | 2.86 ddd (8.5, 3.6, 13.0) | H-4a,H-5',H-6 | |
| 5' | | 2.65 ddd (8.5, 6.5, 13.0) | H-4a,H-5,H-6 | |
| 6 | 153.4 | 6.65 t (8.5) | H-5,H-5' | C-8,CHO |
| 7 | 144.9 | | | |
| 8 | 21.2 | 2.39 dd (14.0, 6.8) | H-8',H-9 | C-6,C-7,CHO |
| 8' | | 2.32 dd (14.0, 5.9) | H-8,H-9 | |
| 9 | 22.5 | 1.83 m | H-8,H-8',H-10,H-10' | C-7 |
| 10 | 28.8 | 2.54 dd (14.3, 6.7) | H-9,H-10' | C-11a,C-11,C-8 |
| 10' | | 2.00 dd (14.3, 6.0) | H-9,H-10 | |
| 11 | 120.6 | | | |
| 11a | 47 | 2.48 dd (11.4, 9.5) | H-1,H-4a | C-18 |
| 12 | 198.2 | | | |
| 13 | 37.6 | 3.40 dd (7.2, 16.1) | H-13',H-14 | C-12,C-15 |
| 13' | | 3.33 dd (7.2, 16.1) | H-13,H-14 | |
| 14 | 116.9 | 5.30 t (7.2) | H-13,H-13' | |
| 15 | 134.9 | | | |
| 16 | 16.7 | 1.68 s | | C-14,C-15,C-17 |
| 17 | 24.5 | 1.75 s | | C-14,C-15,C-16 |
| 18 | 136.0 | 6.98 s | | C-10,C-11,C-11a,18-OAc |
| CHO | 195.8 | 9.27 s | | C-6,C-7,C-8 |
| 1-OAc | 19.1 | 2.05 s | | |
| | 168.9 | | | |
| 18-OAc | 19.0 | 2.10 s | | |
| | 167.8 | | | |

FIG.8

ANTIPROTOZOAL COMPOUND DERIVED FROM COELENTERATA

CROSS REFERENCE TO RELATED APPLICATIONS

The present application is a 35 U.S.C. §371 National Phase Application of International Application Serial No. PCT/JP2011/055715, filed Mar. 10, 2011, which claims priority under the Paris convention to Japanese Patent Application No. 2010-055150 filed on Mar. 11, 2010. The disclosures of each of these applications are incorporated herein by reference in their entirety.

TECHNICAL FIELD

The present invention relates to an antiprotozoal compound derived from coelenterata, and relates more specifically to an antiprotozoal compound derived from *Acanthoprimnoa cristata*.

BACKGROUND ART

Protozoal diseases are serious diseases that remain unresolved. For example, leishmaniasis is an arthropod-borne zoonosis transmitted by sand flies, and is a protozoal disease transmitted to animals by animals for which 100 or more types of vertebrates can act as the reservoir host. Dogs and rodents have a particularly important role in transmission to humans, and the number of infected patients is as many as 12 million people in 88 countries, with 350 million people being exposed to the danger of infection. In recent years, the number of patients is showing an increasing trend, with approximately 2 million new incidences per year, and a severe outbreak has been confirmed in Afghanistan, with 200,000 or more people afflicted, including refugees. *Leishmania* are obligate intracellular protozoan parasites that multiply inside macrophages, and there are 20 or more species known to infect humans. Clinical symptoms in humans can be broadly classified into three groups, with visceral infection being potentially fatal as a result of a disturbance of hematopoiesis, whereas the unsightliness of skin lesions caused by cutaneous and mucocutaneous infections can cause enormous psychological distress. The majority of patients suffering from visceral leishmaniasis, which is the most serious form of the disease, are observed in developing countries, with 90% or more of incidences found within the four countries of India, Bangladesh, Brazil and Sudan. As a result of these circumstances, the WHO has placed leishmaniasis within the category of emergent and uncontrolled tropical infectious disease (category I), and has designated leishmaniasis as one of the ten major tropical infectious diseases requiring urgent measures.

Numerous compounds having unique structures that exhibit high bioactivity have been discovered from marine invertebrates, and they hold much promise as a source of medicines (Patent Document 1). The inventors of the present invention performed antiprotozoal activity screening of marine organisms collected in Japan, with the aim of developing an effective remedy for leishmaniasis. As a result of this screening, they discovered that *Acanthoprimnoa cristata* collected from deep sea locations contained an antiprotozoal substance. The present invention was completed on the basis of this discovery.

PRIOR ART DOCUMENT

Patent Documents

[Patent Document 1] Japanese Unexamined Patent Application Publication No. 2007-161902

DISCLOSURE OF INVENTION

Problems to be Solved by the Invention

Pentavalent antimonials are the first choice drugs for the treatment of all forms of leishmaniasis. The directions for use of these drugs recommended by the WHO involve administration of 20 mg antimony/kg/day for a period of 30 days. The WHO also recommends that in those cases where an initial course of treatment with a pentavalent antimonial yields no noticeable improvement in symptoms, treatment should be shifted to the second choice drug such as pentamidine, aminosidine, amphotericin B or liposomal amphotericin B. One problem of this prescription for leishmaniasis is that both the first choice drugs and the second choice drugs must be administered by injection. It is thought that performing consecutive injections of an antimonial to a patient for one month in a remote location with inadequate medical treatment facilities would prove extremely difficult. Accordingly, there is a need to develop a novel antileishmanial remedy that can be applied without requiring injection. Further, protozoa that are resistant to the aforementioned antimonials have now appeared, and it is only a matter of time before protozoa that are resistant to the second choice drugs also emerge. Accordingly, there is a strong need to develop an antileishmanial remedy that has a novel mechanism of action.

Means to Solve the Problems

The present invention provides a compound having a structure represented by any one of chemical formulas (1) to (3) described below, or a pharmaceutically acceptable salt thereof, wherein within the formulas (1) to (3), $R_1$ represents $R_{10}$— of a formula (4) or $R_{20}$— of a formula (5), $R_2$ represents CHO—, HO—$CH_2$—, $CH_3$—C(=O)— or $CH_3$—CH(—OH)—, $R_3$ represents a hydrogen atom, $CH_3$—C(=O)—, $CH_3$—$CH_2$—C(=O)—, $CH_3$—CH(—OH)— or $CH_3$—$CH_2$—CH(—OH)—, $R_4$ represents a hydrogen atom, $CH_3$—C(=O)—, $CH_3$—$CH_2$—C(=O)—, $CH_3$—CH(—OH)— or $CH_3$—$CH_2$—CH(—OH)—, each of $R_{11}$ and $R_{12}$ independently represents a hydrogen atom, a methyl group or a halogen atom, $R_{13}$ represents —$CH_2$—, —CH(—OH)— or —C(=O)—, each of $R_{21}$ and $R_{22}$ independently represents a hydrogen atom, a methyl group or a halogen atom, $R_{23}$ represents —$CH_2$—, —CH(—OH)— or —C(=O)—, and $R_{24}$ represents a hydrogen atom, a hydroxyl group, a methyl group or a halogen atom.

[Chemical Formula 1]

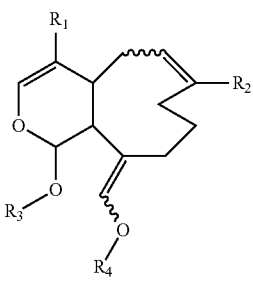
(1)

[Chemical Formula 2]

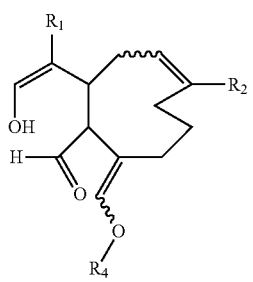
(2)

[Chemical Formula 3]

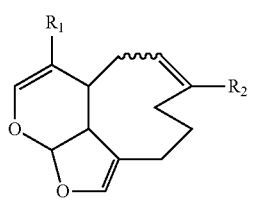
(3)

[Chemical Formula 4]

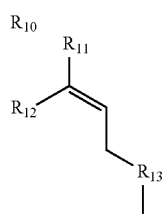
(4)

[Chemical Formula 5]

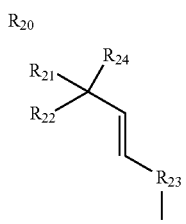
(5)

represents a hydrogen atom, $CH_3—C(=O)—$, $CH_3—CH_2—C(=O)—$, $CH_3—CH(—OH)—$ or $CH_3—CH_2—CH(—OH)—$, $R_4$ represents a hydrogen atom, $CH_3—C(=O)—$, $CH_3—CH_2—C(=O)—$, $CH_3—CH(—OH)—$ or $CH_3—CH_2—CH(—OH)—$, $R_5$ represents a hydrogen atom, $CH_3—C(=O)—$ or $CH_3—CH_2—C(=O)—$, $R_6$ represents a hydrogen atom, $CH_3—C(=O)—$ or $CH_3—CH_2—C(=O)—$, each of $R_{11}$ and $R_{12}$ independently represents a hydrogen atom, a methyl group or a halogen atom, $R_{13}$ represents $—CH_2—$, $—CH(—OH)—$ or $—C(=O)—$, each of $R_{21}$ and $R_{22}$ independently represents a hydrogen atom, a methyl group or a halogen atom, $R_{23}$ represents $—CH_2—$, $—CH(—OH)—$ or $—C(=O)—$, and $R_{24}$ represents a hydrogen atom, a hydroxyl group, a methyl group or a halogen atom.

[Chemical Formula 6]

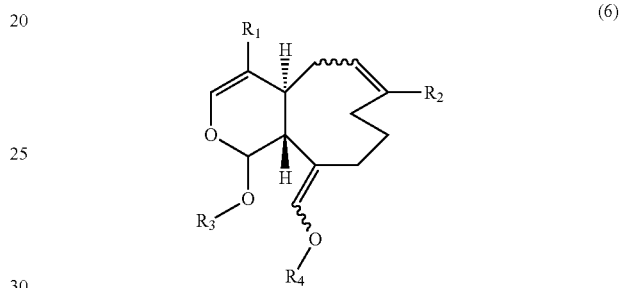
(6)

[Chemical Formula 7]

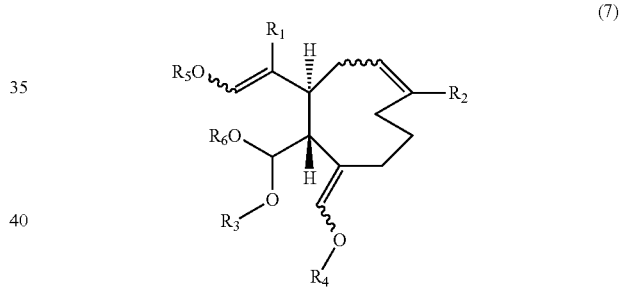
(7)

[Chemical Formula 8]

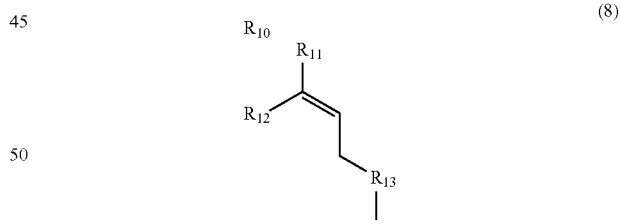
(8)

[Chemical Formula 9]

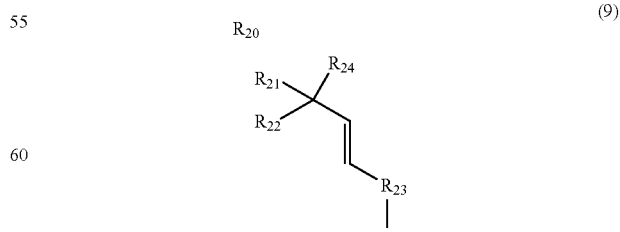
(9)

The present invention provides a compound having a structure represented by a chemical formula (6) or (7) described below, or a pharmaceutically acceptable salt thereof, wherein within the formula (6) or (7), $R_1$ represents $R_{10}—$ of a formula (8) or $R_{20}—$ of a formula (9), $R_2$ represents $CHO—$, $HO—CH_2—$, $CH_3—C(=O)—$ or $CH_3—CH(—OH)—$, $R_3$ The present invention provides a compound having a structure represented by a chemical formula (10) described below, or a pharmaceutically acceptable salt thereof.

[Chemical Formula 10]

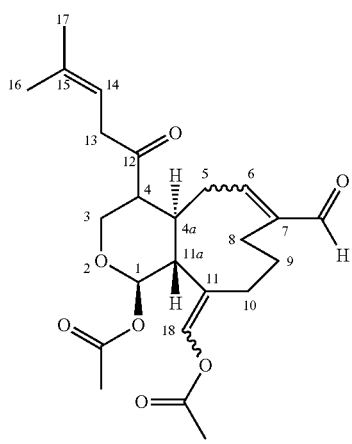

(10)

The present invention also provides a compound or a pharmaceutically acceptable salt thereof which functions as a prodrug that generates a compound of the present invention or a pharmaceutically acceptable salt thereof.

The present invention also provides a pharmaceutical composition for treating a protozoal infection, the composition comprising a compound of the present invention or a pharmaceutically acceptable salt thereof.

The pharmaceutical composition for treating a protozoal infection according to the present invention may comprise at least one medicine selected from the group consisting of pentavalent antimonials, pentamidine, aminosidine, amphotericin B and liposomal amphotericin B, and a compound of the present invention or a pharmaceutically acceptable salt thereof, wherein the at least one medicine and the compound of the present invention or pharmaceutically acceptable salt thereof may be administered either simultaneously or sequentially.

The pharmaceutical composition for treating a protozoal infection according to the present invention may be used as a pharmaceutical composition for treating at least one protozoal infection selected from the group consisting of leishmaniasis, trypanosomiasis and malaria.

In the chemical formulas for the compound of the present invention, in those cases where the formula notation does not distinguish between stereoisomers and/or geometrical isomers, the compound may be either any one of the possible stereoisomers and/or geometrical isomers, or a mixture of two or more of the stereoisomers and/or geometrical isomers. In other words, with the exception of those chemical bonds where a specific steric structure is disclosed, the compound of the present invention is deemed to include all possible optically active substance or racemates, and all diastereoisomers or arbitrary mixtures thereof at all other chemical bonds.

In the present invention, a "halogen" may be any of fluorine, chlorine, bromine and iodine.

Examples of preferred pharmaceutically acceptable salts of the compound of the present invention include acid addition salts such as hydrochlorides, acetates and para-toluenesulfonate salts, base addition salts such as ammonium salts and organic amine salts, and arbitrary hydrates and solvates of peptide derivatives in free form or salt form, but not limited to them.

The pharmaceutical composition of the present invention comprises at least one of the compound of the present invention or a pharmaceutically acceptable salt thereof as an active ingredient. The pharmaceutical composition of the present invention may comprise at least one compound of the present invention or a pharmaceutically acceptable salt thereof, and at least one pharmaceutically acceptable carrier. The pharmaceutical composition of the present invention, which comprises the compound of the present invention or a pharmaceutically acceptable salt thereof as an active ingredient, can be used for the purpose of preventing and/or treating leishmaniasis, and can be administered via parenteral administration such as intravenous administration, subcutaneous administration or intrarectal administration, as well as via oral administration, transmucosal administration or transdermal administration or the like. A variety of dosage forms suitable for these administration pathways will be well known to those skilled in the art, and a person skilled in the art could select an appropriate dosage form suitable for the desired form of administration, and then produce a formulation of the pharmaceutical composition, where necessary using one or more pharmaceutically acceptable carriers or formulation additives that can be used within the field. For example, in the case of transdermal administration, an ointment or other form of applied formulation, or a poultice or other form of patch is ideal. In some cases, a hydrate or solvate of the compound of the present invention or pharmaceutically acceptable salt thereof may be used as the active ingredient of the medicine of the present invention. There are no particular limitations on the dose, and for example, a single dose may be set within a range from 0.1 to 10 mg in the case of transdermal administration or transmucosal administration, or within a range from 1 to 100 mg in the case of an oral administration, with administration being performed 2 or 3 times per day. Alternatively, a dose of approximately 0.1 to 1,000 mg, and preferably approximately 1 to 300 mg, may be typically administered per day to an adult. Further, the dose can also be set in relation to parameters such as the weight, age, genetic type and symptoms of the patient.

The pharmaceutical composition of the present invention may be provided in dosage forms such as tablets, granules (fine grains), capsules, injections (intravenous drips), patches, suppositories, suspensions and emulsions, pastes, ointments, creams, lotions, nasal drops and eye drops, but not limited to them. In some cases, the pharmaceutical composition of the present invention may be converted to a controlled-release form in order to enable sustained release over a long period of time.

The pharmaceutically acceptable carriers or formulation additives included in the pharmaceutical composition of the present invention may include stabilizers, surfactants, solubilizers and adsorbents and the like, but not limited to them. The pharmaceutically acceptable carriers or formulation additives included in the pharmaceutical composition of the present invention are selected in accordance with the dosage form of the pharmaceutical composition of the present invention described above.

In the present invention, the term "protozoa" describes any of various protists that infect humans and other mammals and cause harm to humans, and includes *Leishmania, Plasmodium, Toxoplasma* and *Trypanosoma*, as well as the pathogens that cause protozoal infections such as amoebic dysentery and Chagas disease and the like, but not limited to them.

BRIEF DESCRIPTION OF THE DRAWINGS

FIG. 1 is a flowchart showing separation procedures for an antiprotozoal substance derived from coelenterata.

FIG. 2 is a flowchart showing separation procedures for an antiprotozoal substance derived from coelenterata.

FIG. 8 is a table listing the data resulting from the analysis of cristaxenicin A by NMR (400 MHz, $CD_3OD$).

EMBODIMENTS OF THE INVENTION

Figure 3:
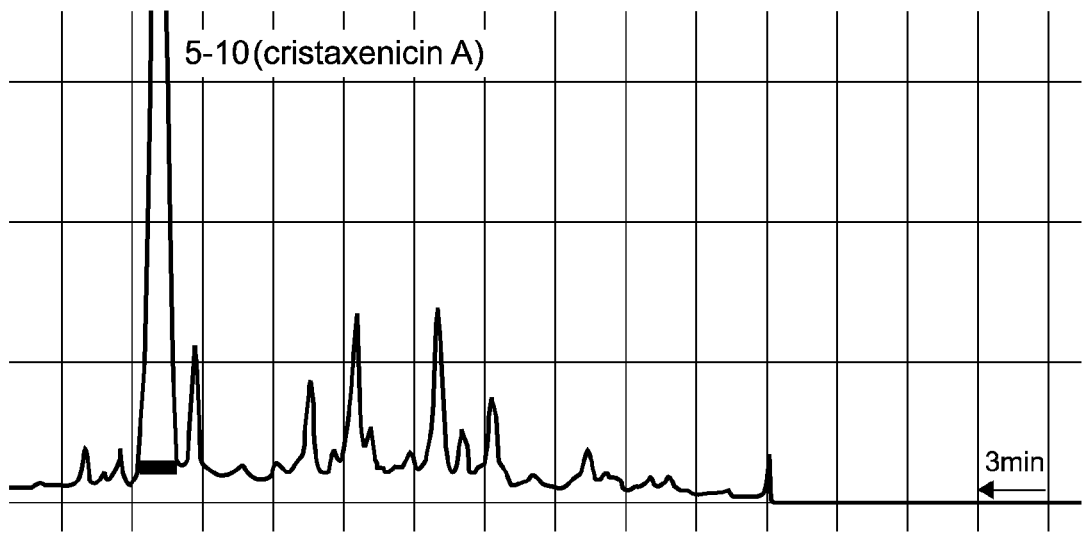
FIG. 3 is a waveform chart showing a reversed phase HPLC separation pattern for components of a fraction 3-2.

The present invention is described below in more detail based on a series of examples, but the present invention is in no way limited by these examples.

Example 1

1. Screening of Antiprotozoal Substances Derived from Japanese Inshore Marine Invertebrates For marine invertebrates collected in Japanese inshore waters, individual specimens of the same species were extracted with methanol, and concentrated, then the extract was subjected to two-layer partitioning using water and chloroform. The dry weights of the crude extracts of the obtained water-soluble fraction and lipid-soluble fraction were measured. Further, conducting the bioactivity tests described below, the antiprotozoal activity against *Leishmania* parasites, and the cytotoxicity against human cervical cancer-derived HeLa cells and mouse lymphoma-derived P388 cells were measured.

2. Bioactivity Tests 2-1 Antileishmanial Activity Test

EGFP transgenic *Leishmania* protozoa (LaEGFP, Okuno T et al., Exp. Anim, 52: 109 (2003)) $1\times10^5$ cells were inoculated into a 96-well plate, and a sample diluted with a culture medium was then added and incubated for 72 hours. Subsequently, the fluorescence intensity within each well was measured using a fluorescence plate reader, and the antileishmanial activity of the test sample was calculated.

2-2 Cytotoxicity Test

A suspension of human cervical cancer-derived HeLa cells and mouse lymphoma-derived P388 cells ($1\times10^4$ cells/mL) 200 µL was dispended into each well of rows A to H, columns 1 to 11 of a 96-well microplate, and the suspension was then incubated for 24 hours at 37° C. Subsequently, 2 µL of a methanol solution of the sample (1 mg/mL) was added to each well of row A, columns 1 to 10 of the 96-well microplate, and 2 µL of adriamycin (1 mg/mL) was added to the well of row A, column 11 as a positive control. Only the culture medium 200 µL was added to each well of rows A to D, column 12, and 200 µL of the aforementioned suspension of $1\times10^4$ cells/mL was added to each well of rows E to H, column 12. Using a multi-channel pipette, 50 µL of the culture medium was aspirated from the well of each column of row A and added to the well of the corresponding column of row B, and then 50 µL of the culture medium was aspirated from the well of each column of row B and added to the well of the corresponding column of row C. These procedures were repeated so that consecutive 5-fold dilutions were achieved in sequence from row A to row H, thereby achieving dilution of the sample in 8 stages. Following culturing for 72 hours, 50 µL of 1 mg/mL PBS solution of MTT (3-[4,5-dimethylthiazol-2-yl]-2,5-diphenyl tetrazolium bromide) was added to each well. Following subsequent incubating for 3 hours, the entire culture medium was removed from each well, and 150 µL of DMSO was added. For each well, the absorbance of the colorimetric substrate dissolved in the DMSO was measured using a multi-well plate reader, and the concentration at which half the cells were inhibited ($IC_{50}$) was determined.

3. Results

The sample of *Acanthoprimnoa cristata* (sample code number: C07110) was dredged at Yakushima Shin-Sone in Kagoshima prefecture (from latitude 29° 46' 55" N, longitude 130° 21' 92" E, depth 138 m to latitude 29° 46' 71" N, longitude 130° 22' 06" E, depth 135 m). The screening results for the sample C07110 and a sample of an unidentified species of *Porifera* screened at the same time (sample code number: S07161) are shown in Table 1.

TABLE 1

| | $IC_{50}$ (µg/mL) | | |
|---|---|---|---|
| | HeLa | P388 | LaEGFP |
| C07110 water-soluble fraction | 50 | 50 | 26.4 |
| C07110 lipid-soluble fraction | 10 | 10 | 1.1 |
| S07161 water-soluble fraction | 0.4 | 0.4 | 6.4 |
| S07161 lipid-soluble fraction | 0.08 | 0.08 | 0.6 |

As shown in Table 1, the $IC_{50}$ value for the lipid-soluble fraction of the sample C07110 against the *Leishmania* parasites was 1.1 µg/mL, whereas the $IC_{50}$ values against the human HeLa cells and mouse P388 cells were both 10 µg/mL. In other words, the antiprotozoal activity of this fraction was approximately 10 times more selective than the cytotoxicity against humans and mice. In comparison, the $IC_{50}$ value for the lipid-soluble fraction of the sample S07161 against the *Leishmania* parasites was 0.6 µg/mL, which represents higher activity than C07110, but the $IC_{50}$ values against the human HeLa cells and mouse P388 cells were both 0.08 µg/mL, which represents a higher activity than the antiprotozoal activity, meaning selectivity is problematic. Accordingly, isolation of the antileishmanial substance from the sample C07110 was undertaken.

Example 2

Isolation of Novel Antiprotozoal Substances

1. Fraction 5-10

Separation procedures for the antiprotozoal substances derived from 90 g of the *Acanthoprimnoa cristata* of the sample C07110 is shown in FIG. 1 and FIG. 2. With reference to FIG. 1, the animal individuals were extracted with methanol, and following concentration, the extract was subjected to two-layer partitioning using water and chloroform. The water layer was further extracted with n-butanol, and the thus obtained n-butanol layer was mixed with the chloroform layer and concentrated. This extract fraction was subjected to Kupchan partitioning (Kupchan, S. M. et al., J. Org. Chem., 38: 178 to 179 (1973)), yielding an n-hexane fraction, a chloroform fraction, and a 60% methanol-soluble fraction 2-3. The fraction 2-3 was separated by ODS flash column chromatography [50% methanol, 70% methanol, 70% acetonitrile, 85% acetonitrile, methanol, chloroform/methanol/water (6:4:1)]. Of the resulting fractions, the 70% methanol fraction, which showed strong antileishmanial activity (fraction 3-2, 76.8 mg, of which 71.2 mg was used for further separation), was subjected to a final separation by reversed phase HPLC using a $C_{18}$ column (70 to 90% methanol). FIG. 3 is a waveform chart showing the results obtained when the fraction 3-2 was separated using a column of diameter 2 cm and length 25 cm packed with COSMOSIL-5$C_{18}$-AR-II, under conditions including a flow rate of 6 mL/minute and a methanol gradient from 70% to 90%. The vertical axis of FIG. 3 represents the relative value of the absorbance of ultraviolet light of 220 nm, and the horizontal axis of FIG. 3 indicates increasing retention time from right to left. The arrow along the horizontal axis indicates 3 minutes. The yield of a peak fraction 5-10 indicated by the bold line was 19.7 mg. Further analysis of the fraction 5-10 indicated that the fraction was composed of a single substance. Accordingly, the fraction 5-10 was subjected to instrumental analysis.

2. Fractions 13-2 and 13-4

Figure 4:
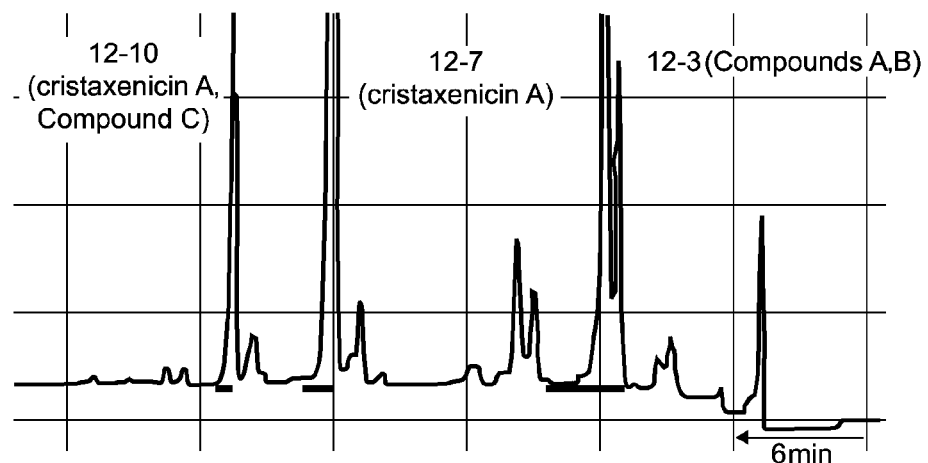
FIG. 4 is a waveform chart showing a reversed phase HPLC separation pattern for components of a fraction 3-3.
Figure 5:
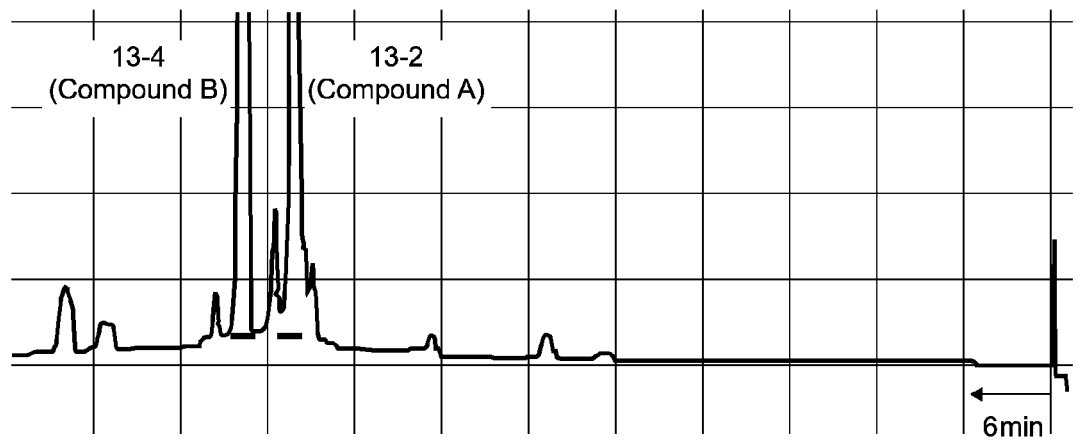
FIG. 5 is a waveform chart showing a reversed phase HPLC separation pattern for components of a fraction 12-3.

The 70% acetonitrile fraction (3-3) from the aforementioned ODS flash column chromatography was confirmed as having similar activity to that of the 70% methanol fraction (3-2) described above. The results of performing separation by reversed phase HPLC using a $C_{18}$ column (70 to 90% methanol) are shown in FIG. 4. FIG. 4 is a waveform chart showing the results obtained when the fraction 3-3 was separated using a column of diameter 2 cm and length 25 cm packed with COSMOSIL-5$C_{18}$-AR-II, under conditions including a flow rate of 8 mL/minute and a methanol gradient from 70% to 90%. The vertical axis of FIG. 4 represents the relative value of the absorbance of ultraviolet light of 220 nm, and the horizontal axis of FIG. 4 indicates increasing retention time from right to left. The arrow along the horizontal axis indicates 6 minutes. The yields of peak fractions 12-3, 12-7 and 12-10 indicated by the bold lines were 2.5 mg, 3.4 mg and 1.2 mg respectively. A procedure for separating the antiprotozoal components from the fractions 12-3, 12-7 and 12-10 is shown in FIG. 2. With reference to FIG. 4, the fractions 12-3, 12-7 and 12-10 were separated by reversed phase HPLC using a $C_{18}$ column The fraction 12-3 was separated using a column of diameter 1 cm and length 25 cm packed with COSMOSIL-5$C_{18}$-AR-II, under conditions including a flow rate of 2 mL/minute and a methanol gradient from 50% to 70%. FIG. 5 is a waveform chart showing the results obtained when the fraction 12-3 was separated using a column of diameter 1 cm and length 25 cm packed with COSMOSIL-5$C_{18}$-AR-II, under conditions including a flow rate of 2 mL/minute and a methanol gradient from 50% to 70%. The vertical axis of FIG. 5 represents the relative value of the absorbance of ultraviolet light of 220 nm, and the horizontal axis of FIG. 5 indicates increasing retention time from right to left. The arrow along the horizontal axis indicates 6 minutes. Approximately half of the yield of the fraction 12-3 was used in the column separation, and the yields of peak fractions 13-2 and 13-4 indicated by the bold lines were 0.2 mg and 0.3 mg respectively. The peak fractions 13-2 and 13-4 both exhibited antiprotozoal activity. Further analysis of the fractions 13-2 and 13-4 indicated (data not shown) that the fractions were each composed of a single substance. Accordingly, the fractions 13-2 and 13-4 were subjected to instrumental analysis.

3. Fraction 12-7

Further analysis of the fraction 12-7 indicated (data not shown) that the fraction was composed of a single substance. Accordingly, the fraction 12-7 was subjected to instrumental analysis.

4. Fractions 14-1 and 14-2

Figure 6:
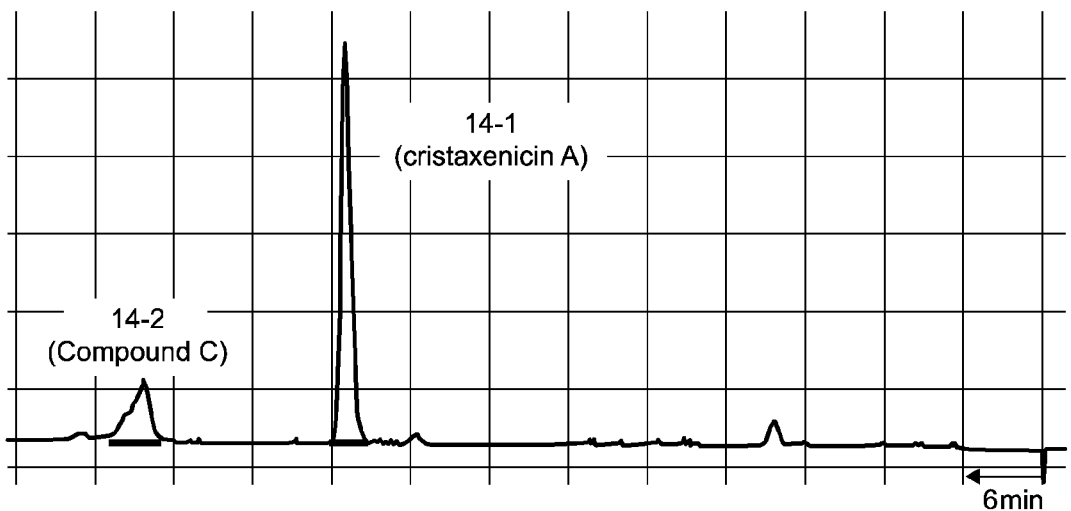
FIG. 6 is a waveform chart showing a reversed phase HPLC separation pattern for components of a fraction 12-10.

The fraction 12-10 was separated using a column of diameter 1 cm and length 25 cm packed with COSMOSIL-5$C_{18}$-AR-II, under conditions including a flow rate of 2 mL/minute and a methanol gradient from 65% to 75%. FIG. 6 is a waveform chart showing the results obtained when the fraction 12-10 was separated using a column of diameter 1 cm and length 25 cm packed with COSMOSIL-5$C_{18}$-AR-II, under conditions including a flow rate of 2 mL/minute and a methanol gradient from 65% to 75%. The vertical axis of FIG. 6 represents the relative value of the absorbance of ultraviolet light of 220 nm, and the horizontal axis of FIG. 6 indicates increasing retention time from right to left. The arrow along the horizontal axis indicates 6 minutes. Approximately half of the yield of the fraction 12-10 was used in the column separation, and the yields of peak fractions 14-1 and 14-2 indicated by the bold lines were 0.8 mg and 0.2 mg respectively. The peak fractions 14-1 and 14-2 both exhibited antiprotozoal activity. Further analysis of the fractions 14-1 and 14-2 indicated (data not shown) that the fractions were each composed of a single substance. Accordingly, the fractions 14-1 and 14-2 were subjected to instrumental analysis.

Example 3

Structural Analysis of Novel Antiprotozoal Substances

1. Fraction 5-10

The instrumental analysis data for the antileishmanial substance fraction 5-10 was as follows. $[\alpha]^{21.7}_D$+90.5° (c 0.22, MeOH); IR 2931, 1755, 1681, 1616, 1454, 1371, 1340, 1209, 1176, 1108, 1076, 1015 $cm^{-1}$; UV (MeOH) 231 nm (log ε 4.28); FABMS m/z 431 $[M+H]^+$, 453 $[M+Na]^+$; HRFABMS m/z 431.2089 (calculated for $C_{24}H_{31}O_7$ 431.2070)

Figure 7:
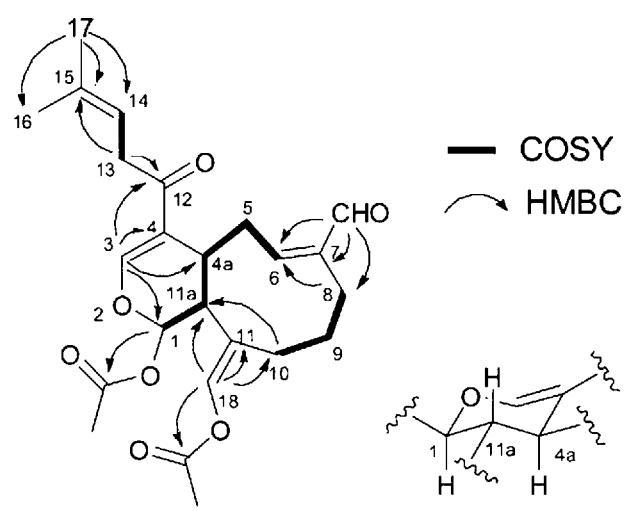
FIG. 7 is a diagram showing the results of COSY and HMBC correlations for cristaxenicin A.

The results of high resolution fast atom bombardment mass spectrometry (HRFABMS) revealed that the molecular formula of the antileishmanial substance isolated as the fraction 5-10 was $C_{24}H_{30}O_7$. The results of $^1$H NMR spectral analysis indicated that the antileishmanial substance had two acetyl groups ($\delta_H$ 2.10, 2.05), one aldehyde group ($\delta_H$ 9.27), and two methyl groups ($\delta_H$ 1.75, 1.68). The results of $^{13}$C NMR spectral analysis confirmed 24 carbon atoms, and revealed that the antileishmanial substance had a conjugated ketone group (δ 198.2). The results of $^1$H-$^1$H correlation two-dimensional NMR spectral analysis (COSY) revealed three spin systems. The results of HMBC analysis revealed correlations from the aldehyde group to C-6 (δ 153.4), C-7 (δ 144.9) and C-8 (δ 21.2), confirming that in the antileishmanial substance, the aldehyde group was bonded to C-7. Further, a correlation was observed from H-18 ($\delta_H$ 6.98) to the carbonyl carbon of one of the acetyl groups, confirming that one of the acetyl groups of the antileishmanial substance was bonded to C-18 via an oxygen atom. Furthermore, correlations were also observed from H-18 to C-10 (δ 28.8), C-11 (δ 120.6) and C-11a, confirming that the two spin systems were linked, forming a 9-membered ring. On the other hand, a correlation was observed from H-1 ($\delta_H$ 5.86) to an acetyl group, confirming that the other acetyl group was bonded to C-1 via an oxygen atom. Based on correlations from H-3 to C-4 (δ 120.2), C-4a (δ 35.9) and C-1 (δ 94.5), and the chemical shifts of H-3 ($\delta_H$ 7.68) and H-1 ($\delta_H$ 5.86), it was evident that the antileishmanial substance had a dihydropyran cyclic structure. Correlations were observed from the aforementioned two methyl groups (H-16 and H-17) to C-15 (δ 134.9) and C-14 (δ 116.9), confirming that the two methyl groups were bonded to C-15. Correlations were also observed from H-3, H-13a and H-13b to C-12 (δ 198.2), confirming that the aforementioned conjugated ketone group was positioned between C-13 and C-4. FIG. 7 shows the results of the COSY and HMBC correlations. FIG. 8 shows the data resulting from analysis of the antileishmanial substance by NMR (400 MHz, $CD_3OD$). Based on the above analysis results, the antileishmanial substance was identified as a novel Xenicane-type terpenoid having a structure represented by a chemical formula (11) described below. This substance was named cristaxenicin A after the species name of its bioresource.

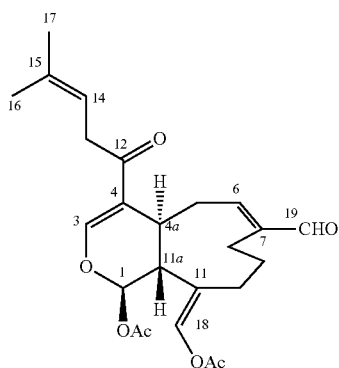 [SMILES: CC(=O)O/C=C1\CCC/C(C=O)=C\C[C@@H]2C(C(=O)CC=C(C)C)=CO[C@H](OC(C)=O)[C@@H]12]

In terms of the relative configuration of the antileishmanial substance, the existence of large coupling constants between H-11a, H-1 and H-4a (J=9.5, 11.4 Hz) suggests that these are axial protons, and exist in mutually anti relationships.

2. Fraction 12-7

When reversed phase HPLC was performed using the $C_{18}$ column described in the example 2, the fraction 12-7 had the same retention time as cristaxenicin A, and it was therefore concluded that the structure was also the same.

3. Fractions 13-2 and 13-4

The yields of the fractions 13-2 and 13-4 were small. From FIG. 5, it is clear that the fraction 12-3 contained no significant components other than the fractions 13-2 and 13-4, and therefore the $^1$H NMR spectrum of the fraction 12-3 was measured as a mixture of the fractions 13-2 and 13-4. In the following description, the components of the fractions 13-2 and 13-4 are referred to as "compound A" and "compound B" respectively. The results of the NMR measurement of the fraction 12-3 revealed similar peak groups to cristaxenicin A, and therefore it was assumed that the components of the fraction 12-3, namely the compounds A and B, were analogs of cristaxenicin A. The results of ESIMS measurement revealed peaks at 469.2 $[M+Na]^+$ and 485.2 $[M+K]^+$, and it was therefore presumed that the molecular formula was $C_{24}H_{30}O_8$, with one more oxygen atom than cristaxenicin A. Comparison of the $^1$H NMR spectrum of the fraction 12-3 with that of cristaxenicin A revealed that the peaks observed for H-13 ($\delta_H$ 3.33/3.40) and H-14 ($\delta_H$ 5.30) of cristaxenicin A had disappeared, and had been replaced with two doublet olefin peaks [$\delta_H$ 6.68 d (15.8 Hz), 6.91 d (15.8 Hz)] observed at the low-field side. Further, it was also clear that the two singlets attributable to the methyl groups at the side chain terminal of cristaxenicin A had undergone a high-field shift (1.36 s, 1.37 s). These analysis results suggested that although the compounds A and B were analogs of cristaxenicin A, they differed from cristaxenicin A in terms of the structure of part of the side chain bonded to the pyran ring.

The results of $^{13}$C NMR, HMQC and HMBC spectral analyses of the compounds A and B confirmed that the ketone group had undergone a high-field shift (δ near 190), and that there was an HMBC correlation from the doublet olefin peaks [$\delta_H$ 6.68 d (15.8 Hz), 6.91 d (15.8 Hz)] to the ketone group, and it was therefore clear that a double bond was formed between 12C-13 and C-14, and was conjugated with the ketone of C-12. Based on the existence of HMBC correlations from C-14 and the protons of the two singlet methyl groups C-16 and C-17 to the carbon signal at δ 82.5, it was evident that this carbon signal was attributable to C-15. These HMBC correlations are shown below in chemical formula 12. Based on the chemical shift value (δ 82.5), it was assumed that a hydroxyl group was attached to C-15. The same unit as this presumed partial structure exists in the previously reported tsitsixenicin C (Hooper, G. J. and Davies-Coleman, M., Tetrahedron, 51: 9973 (1995)), and comparison of the $^1$H NMR and $^{13}$C NMR spectra revealed that the spectra were substantially identical (the results for compounds A and B are shown below in chemical formula 13, and the results for tsitsixenicin C are described in chemical formula 14). Based on the above results, it was confirmed that one of the compounds A and B had the structure shown below in chemical formula 15.

[Chemical Formula 12]

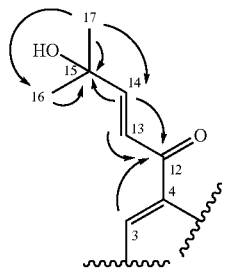

[Chemical Formula 13]

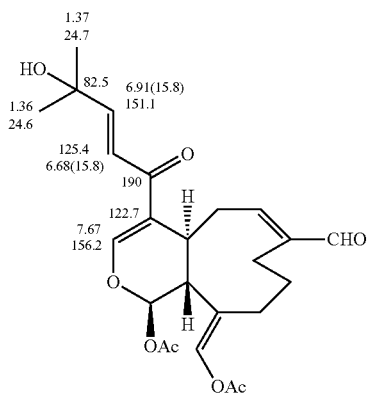

-continued

[Chemical Formula 14]

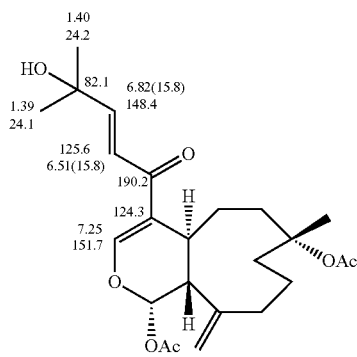

[Chemical Formula 15]

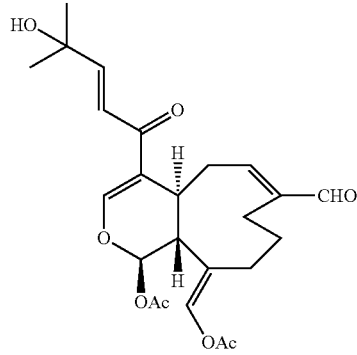

4. Fractions 14-1 and 14-2

Comparison of the results of NMR analaysis confirmed that the fraction 14-1 was the same as cristaxenicin A. The proton NMR analysis results for the fraction 14-2 differed from those of the fraction 14-1, indicating that the structure of the component of the fraction 14-2 (hereafter referred to as "compound C") was not the same as that of the fraction 14-1.

Example 4

Bioactivity of Novel Antiprotozoal Substances

1. Antileishmanial Activity Test

EGFP transgenic *Leishmania* protozoa (LaEGFP, Okuno T et al., Exp. Anim, 52: 109 (2003)) 1×10$^5$ cells were inoculated into a 96-well plate, and a sample diluted with a culture medium was then added and incubated for 72 hours. Subsequently, the fluorescence intensity within each well was measured using a fluorescence plate reader, and the antileishmanial activity of the test sample was calculated.

2. Antitrypanosomal Activity Test

*Trypanosoma congolense* (bloodstream form) 2×10$^5$ cells were inoculated into a 96-well plate, and a sample diluted with a culture medium was then added and cultured for 48 hours. Subsequently, 10 µL of TetraColor ONE (Seikagaku Biobusiness Corporation) was added to each well to measure the viable cell count, and after 4 hours, the absorbance at 450 nm was measured.

3. Antiplasmodial Activity Test

Synchronized 0.5% ring stage *Plasmodium falciparum* K-1 strain 90 µL was added to each well of a 96-well plate, and a sample diluted with a culture medium was then added and incubated for 48 hours. Subsequently, 100 µL of a mixed solution prepared by adding 0.2 µL of SYBR GREEN to 1 mL of lysis buffer (20 mM Tris (pH 7.5), 5 mM EDTA, 0.008% (wt/vol) saponin, 0.08% (vol/vol) Triton X-100) was added to each well, and stirred with a vortex mixer. Following standing for 1 hour in a dark place, the fluorescence was measured with a fluorescence plate reader, using an excitation wavelength of 485 nm and a detection wavelength of 530 nm.

4. Cytotoxicity Test

A suspension of human cervical cancer-derived HeLa cells, human promyelocytic leukemia-derived HL-60 cells, and mouse lymphoma-derived P388 cells (1×10$^4$ cells/mL) 200 µL was dispended into each well of rows A to H, columns 1 to 11 of a 96-well microplate, and the suspension was then incubated for 24 hours at 37° C. Subsequently, 2 µL of a methanol solution of the sample (1 mg/mL) was added to each well of row A, columns 1 to 10 of the 96-well microplate, and 2 µL of adriamycin (1 mg/mL) was added to the well of row A, column 11 as a positive control. Only the culture medium 200 µL was added to each well of rows A to D, column 12, and 200 µL of the aforementioned suspension of 1×10$^4$ cells/mL was added to each well of rows E to H, column 12. Using a multi-channel pipette, 50 µL of the culture medium was aspirated from the well of each column of row A and added to the well of the corresponding column of row B, and then 50 µL of the culture medium was aspirated from the well of each column of row B and added to the well of the corresponding column of row C. This procedure was repeated so that consecutive 5-fold dilutions were achieved in sequence from row A to row H, thereby achieving dilution of the sample in 8 stages. Following culturing for 72 hours, 50 µL of 1 mg/mL PBS solution of MTT (3-[4,5-dimethylthiazol-2-yl]-2,5-diphenyl tetrazolium bromide) was added to each well. Following subsequent incubating for 3 hours, the entire culture medium was removed from each well, and 150 µL of DMSO was added. For each well, the absorbance of the colorimetric substrate dissolved in the DMSO was measured using a multi-well plate reader, and the concentration at which half the cells were inhibited (IC$_{50}$) was determined.

5. Results

The IC$_{50}$ value for cristaxenicin A against the LaEGFP was 36 ng/mL. This is higher than the IC$_{50}$ value for amphotericin B (approximately 20 ng/mL), which is one of the second choice drugs for leishmaniasis. The IC$_{50}$ value against *Leishmania* for pentavalent antimonial, which is the first choice drug for leishmaniasis, has been reported as 9 µg/mL (Vermeersch, M. et al., Antimicrob. Agents Chemother., 53: 3855 (2009)), meaning cristaxenicin A exhibits much higher activity.

The IC$_{50}$ value for cristaxenicin A against the *T. congolense* was 107 ng/mL. This is lower than the IC$_{50}$ value for amphotericin B (811 ng/mL), which has been reported as having activity against *Trypanosoma* protozoa. The IC$_{50}$ value against *T. congolense* for diminazene, which is a first choice drug for livestock trypanosomiasis, has been reported as 0.1 to 1 µg/mL (Kaminsky et al., Vet Parsitol 52: 235 (1994)), indicating that cristaxenicin A also exhibits high activity against *Trypanosoma* protozoa. Furthermore, the IC$_{50}$ value for cristaxenicin A against the *Plasmodium falciparum* K-1 strain was 4.6 µg/mL. The antileishmanial activity IC$_{50}$ values for the fraction 12-3 (a mixture of the compounds A and B) and the fraction 12-10 (a mixture of cristaxenicin A and the compound C) were 1,209 ng/mL and 286 ng/mL respectively.

The IC$_{50}$ values for cristaxenicin A against the human cervical cancer-derived HeLa cells, human promyelocytic leukemia-derived HL-60 cells, and mouse lymphoma-derived P388 cells were 2.0 µg/mL, 0.727 µg/mL and 0.89 µg/mL respectively. Accordingly, cristaxenicin A exhibits a selective toxicity against *Leishmania* that is approximately 20 to 56 times that observed against human cultured cells.

The invention claimed is:
1. A compound having a structure represented by a chemical formula described below:

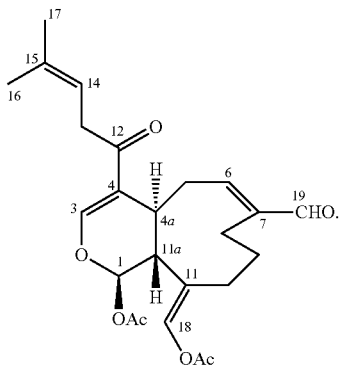 [SMILES: CC(=O)O/C=C1\CCC/C(C=O)=C\C[C@@H]2C(C(=O)CC=C(C)C)=CO[C@H](OC(C)=O)[C@@H]12]

2. A pharmaceutical composition for treating a protozoal infection, the composition comprising the compound according to claim 1.

3. The pharmaceutical composition for treating a protozoal infection according to claim 2, wherein the protozoal infection is at least one protozoal infection selected from the group consisting of leishmaniasis, trypanosomiasis and malaria.

4. A pharmaceutical composition for treating a protozoal infection, the composition comprising at least one medicine selected from the group consisting of pentavalent antimonials, pentamidine, aminosidine, amphotericin B and liposomal amphotericin B, and the compound according to claim 1, wherein the at least one medicine and the compound according to claim 1 are administered either simultaneously or sequentially.

5. The pharmaceutical composition for treating a protozoal infection according to claim 4, wherein the protozoal infection is at least one protozoal infection selected from the group consisting of leishmaniasis, trypanosomiasis and malaria.

* * * * *